(12) United States Patent
Bianca

(10) Patent No.: US 7,303,532 B2
(45) Date of Patent: Dec. 4, 2007

(54) TRACE EVIDENCE COLLECTION METHOD AND APPARATUS

(76) Inventor: Salvatore J. Bianca, 19229 Middletown Rd., Parkton, MD (US) 21120

( * ) Notice: Subject to any disclaimer, the term of this patent is extended or adjusted under 35 U.S.C. 154(b) by 843 days.

(21) Appl. No.: 10/769,443

(22) Filed: Jan. 30, 2004

(65) Prior Publication Data

US 2005/0169800 A1 Aug. 4, 2005

(51) Int. Cl.
*A61B 10/00* (2006.01)
(52) U.S. Cl. ............... 600/572; 435/307.1; 435/309.1; 206/438; 206/210; 206/219; 206/363; 74/25
(58) Field of Classification Search ................. 436/174
See application file for complete search history.

(56) References Cited

U.S. PATENT DOCUMENTS

| | | | |
|---|---|---|---|
| 4,211,323 A | 7/1980 | Olsen | 206/210 |
| 4,707,450 A | 11/1987 | Nason | 435/295 |
| 4,803,998 A | 2/1989 | Kexes et al. | 128/759 |
| 5,477,863 A | 12/1995 | Grant | 128/759 |
| 5,874,045 A | 2/1999 | Chisum | 422/58 |
| 6,171,260 B1 | 1/2001 | Hochmeister et al. | 600/572 |

OTHER PUBLICATIONS

"Crime Investigation," Paul Kirk, John Wiley & Sons. Inc., pp. 23-25 (1953).

*Primary Examiner*—Walter D. Griffin
*Assistant Examiner*—Bobby Ramdhanie
(74) *Attorney, Agent, or Firm*—Larry J. Guffey

(57) ABSTRACT

A method for collecting air-transportable evidence samples from objects and clothing: (a) utilizes a collection tube having open upstream and downstream ends, and at a point between these ends a constriction in the cross-sectional area of the tube, (b) utilizes an applicator stick having proximate and distal ends, the length of this stick being less than the length of the collection tube between its constriction and downstream end, and the distal end of this stick having an air permeable tip, (c) places the proximate end of the applicator stick in the upstream end of tube, (d) orients the stick so that its tip is proximate the tube constriction, and (e) imposes a suction force on the downstream end of the tube so that any air-transportable evidence sample proximate the upstream end of the collection tube is sucked into the tube and becomes lodged on the stick's tip.

15 Claims, 4 Drawing Sheets

TRACE EVIDENCE COLLECTION METHOD AND APPARATUS

BACKGROUND OF THE INVENTION

1. Field of the Invention

The present invention generally relates to the sampling of non-liquid materials and forensic apparatus and methods. More particularly, this invention relates to an apparatus and method for collecting trace amounts of evidence from a crime scene.

2. Description of the Related Art

Crime scene evidence such as that collected on sample swabs often provides critical information necessary for identification of suspects and the determination of guilt or innocence of accused individuals at trial. Often, the evidence is very small and may be dispersed over a comparatively large area (e.g., a flake of skin in the sweat band of a hat, a fiber in a piece of clothing), thus requiring the use of some sort of sampling method to be used over the area to be searched for evidence.

It is a common practice for forensic personnel to use swab applicators in these circumstances. Commonly, the applicator has an elongate shaft made of wood or a plastics material. At the tip end of the shaft is a cotton or synthetic swab. Such applicators are typically kept in a sterile package until they are to be used. After they are used to collect evidence samples, they are placed in a sealed transport or storage container. For examples of such sample collection devices, see U.S. Pat. Nos. 6,171,260, 5,874,045, 5,477,863, 4,803,998, 4,707,450, and 4,211,323.

One using such applicators when searching for trace amounts of evidence on an object will typically touch the swab end of the applicator to various spots within the object's area of interest in the hope of collecting a sample that contains evidence. This technique suffers from several deficiencies. This sampling method will typically cover only a relatively small part of the to-be-searched area and can result in valuable evidence not being collected. By touching the same swabs to many different areas, the possibility that the swab can cross-contaminate various parts of a crime scene, or even destroy other valuable evidence (e.g., fingerprints). Additionally, the object being searched (e.g., the inside of a glove) may have to be handled extensively in order to fully expose all the parts of the object which are to be searched. However, any excessive handling of the object runs the risk of deteriorating the evidentiary value of the object.

In an attempt to more thoroughly search the total surface area of an object, it is known to use a vacuum sweeper with special filter attachments. See FIG. 1 from "Crime Investigation," Paul Kirk, John Wiley & Sons. Inc., 1953 for an example of such a filter attachment. It consists of two, open ended cylinders of clear plastic with hose connections which are joined together at their otherwise open ends. Mounted in one of the cylinders is a metal screen on which is placed a filter paper on which samples are collected.

Such sweepers have several disadvantages. They are often of relatively large size which can make them awkward to transport and use at a crime site. They were developed to collect relatively large particles (e.g., hair and fiber) and are not really useful in collecting small particle (e.g., clumps of skin cells for DNA testing) samples. They are also generally sized such that they are used with relatively large intake nozzles which can make evidence collection from a small, inaccessible object difficult, if not impossible. Additionally, the collection chamber of such sweepers will typically not be adequately cleaned between uses and presents the possibility of the cross-contamination of collected samples.

Thus, despite the prior art in this area, there still exists a need for better trace evidence collection apparatuses and methods.

3. Objects and Advantages

There has been summarized above, rather broadly, the prior art that is related to the present invention in order that the context of the present invention may be better understood and appreciated. In this regard, it is instructive to also consider the objects and advantages of the present invention.

An object of the present invention is to provide a better method and apparatus for collecting air-transportable, trace evidence samples.

It is another object of the present invention to provide a trace evidence collection method and apparatus that requires minimum handling of an object which is to be searched for evidence.

It is yet another object of the present invention to provide a trace evidence collection method and apparatus that allows for a more complete examination of the surface area of an object which is to be searched for evidence.

It also is an object of the present invention to provide a trace evidence collection method and apparatus that presents minimal chance of its use contaminating or destroying any crime scene evidence.

It is an object of the present invention to provide a trace evidence collection method and apparatus that is especially well suited for collecting those small particle samples that may be candidates for DNA testing.

Other objects and advantages of the present invention will become readily apparent as the invention is better understood by reference to the accompanying drawings and the detailed description that follows.

SUMMARY OF THE INVENTION

The present invention is generally directed to satisfying the needs set forth above and overcoming the limitations and problems identified with prior systems and methods for collecting trace amounts of evidence which may be spread over a relatively large surface area.

In accordance with one preferred embodiment, the present invention takes the form of a method for collecting air-transportable evidence samples from objects and clothing. The steps of this method include: (a) utilizing a collection tube having open upstream and downstream ends, and at a point between these ends a constriction in the cross-sectional area of the tube, (b) utilizing an applicator stick having proximate and distal ends, the length of this stick being less than the length of the collection tube between its constriction and downstream end, and the distal end of this stick having an air permeable tip, (c) placing the proximate end of the applicator stick in the upstream end of tube, (d) orienting the stick so that its tip is proximate the tube constriction, and (e) imposing a suction force on the downstream end of the tube so that any air-transportable evidence sample proximate the upstream end of the collection tube is sucked into the tube and becomes lodged on the stick's tip.

Thus, there has been summarized above, rather broadly, the present invention in order that the detailed description that follows may be better understood and appreciated. There are, of course, additional features of the invention that will be described hereinafter and which will form the subject matter of any eventual claims to this invention.

DESCRIPTION OF THE PREFERRED EMBODIMENT

Figure 1:
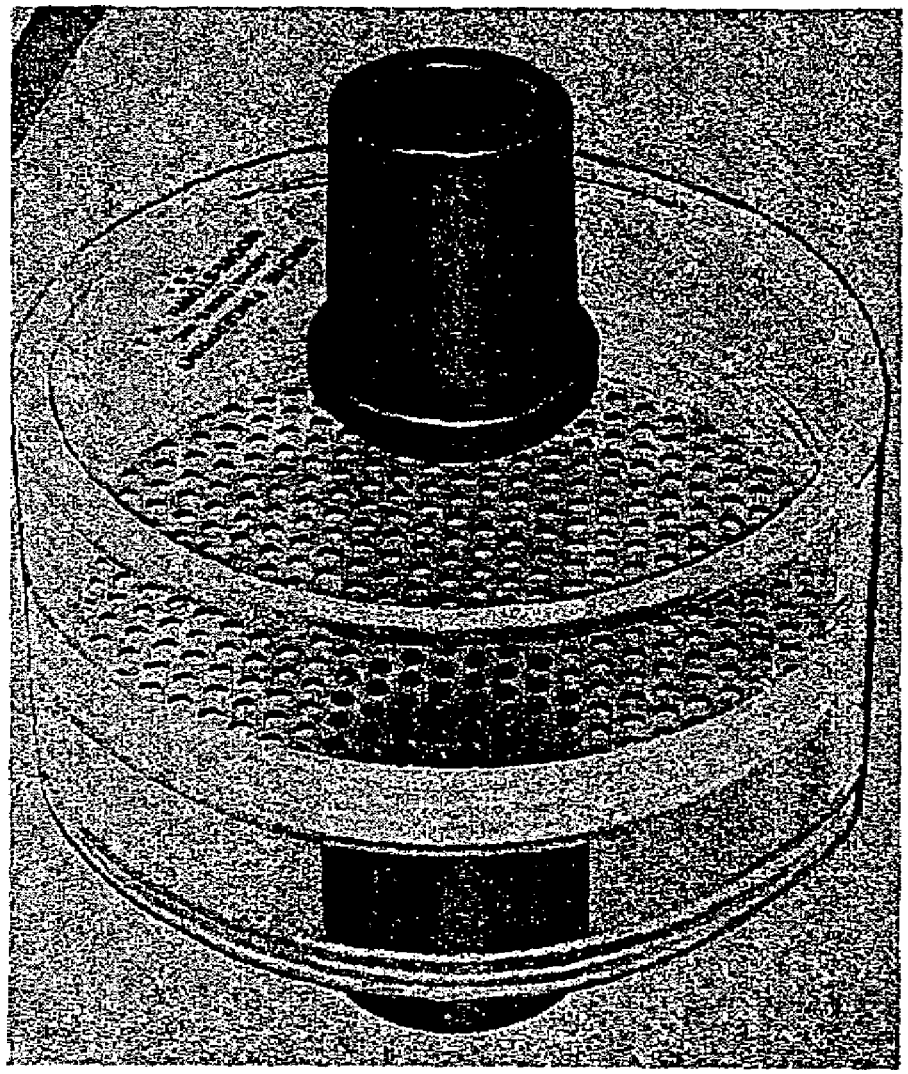
FIG. 1 shows a prior art filter attachment that is used with a vacuum sweeper for the purpose of collecting trace evidence samples.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

Figure 2:
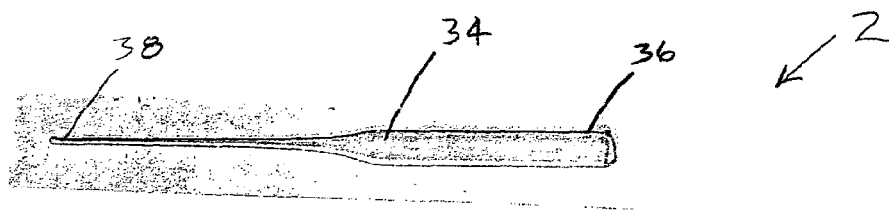
FIG. 2 shows an exploded view of the elements that comprise a preferred embodiment of the present invention.
Figure 2:
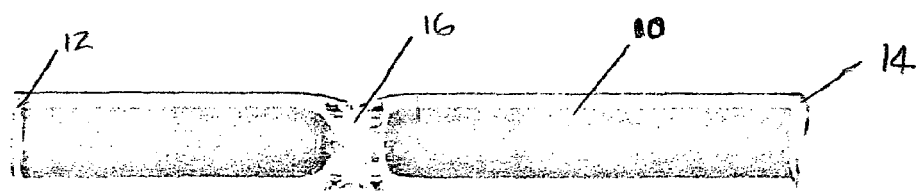
Figure 2:
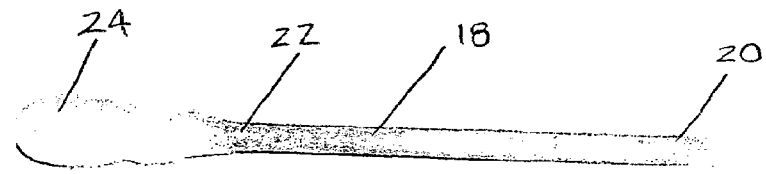
Figure 2:
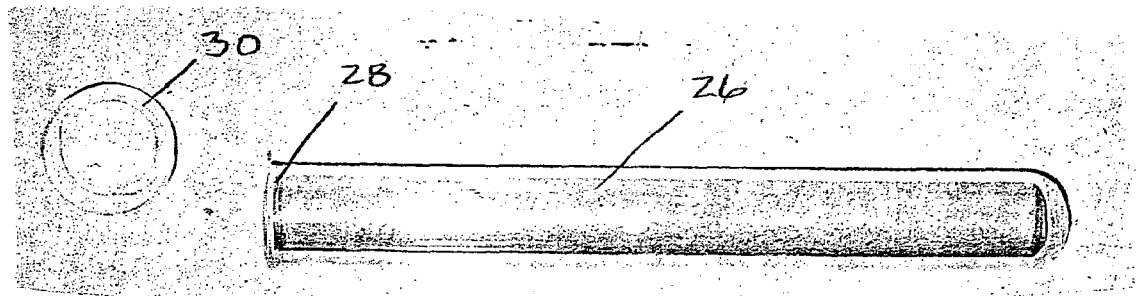

Referring now to the drawings wherein are shown preferred embodiments and wherein like reference numerals designate like elements throughout, as represented in FIG. 2, one embodiment of the present invention takes the form of an apparatus 2 for collecting air-transportable, trace evidence samples from objects and clothing. This embodiment consists of a disposable collection tube 10, an applicator stick 18 with a cotton tip 24 on its distal 22 end, and a test tube and its cap.

The collection tube 10 has a specific cross-sectional area and open upstream 12 and downstream 14 ends. At a specified point between these ends, a specified diameter constriction 16 exists in this tube's cross-sectional area.

The applicator stick 18 of this apparatus has proximate 20 and distal 22 ends, and an air permeable, specified diameter, cotton tip 24 located on the stick's distal 22 end. The diameter of this tip 24 is less than the diameter of the pipette tube 10 and greater than the diameter of the tube's constriction 16. The length of this stick 18 is less than the length of the pipette tube 10 between its constriction 16 and its downstream 14 end.

Figure 3:
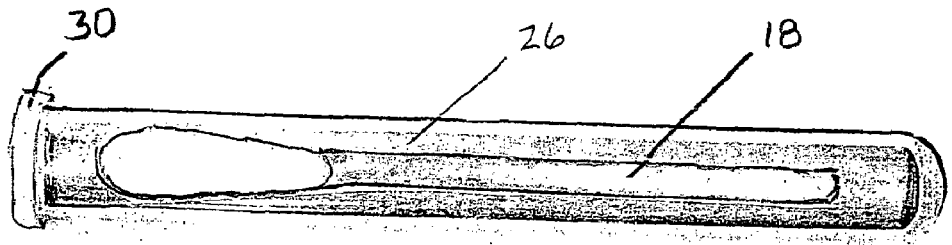
FIG. 3 shows an applicator stick which is suitable for use with the a preferred embodiment of the present invention being stored in a transparent, capped test tube.

A standard test tube 26 or storage vial has a cap 30 for closing the tube's open end 28. and can serve as a storage device for applicator stick 18 which has been used in the apparatus 2 to collect trace evidence samples. The diameter and length of this test tube 26 is such as to allow the applicator stick 18 to be stored in the test tube 26. See FIG. 3 where an applicator stick 18 is seen to be contained within a transparent tube 26.

Figure 4:
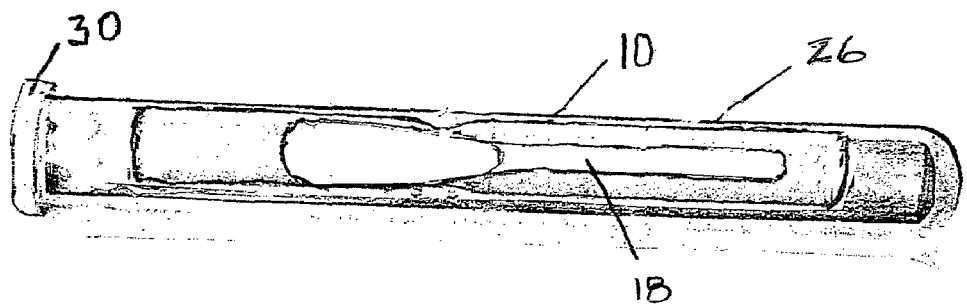
FIG. 4 shows an applicator stick and its collection tube both being stored in a transparent, capped test tube.

Alternatively, the test tube 26 or storage vial can be sized so that it can contain both the applicator stick 18 and its collection tube 10. The advantage of this technique is that it minimizes handling of the individual applicator sticks which could result in the loss of some of the collected trace evidence samples. See FIG. 4.

Figure 5:
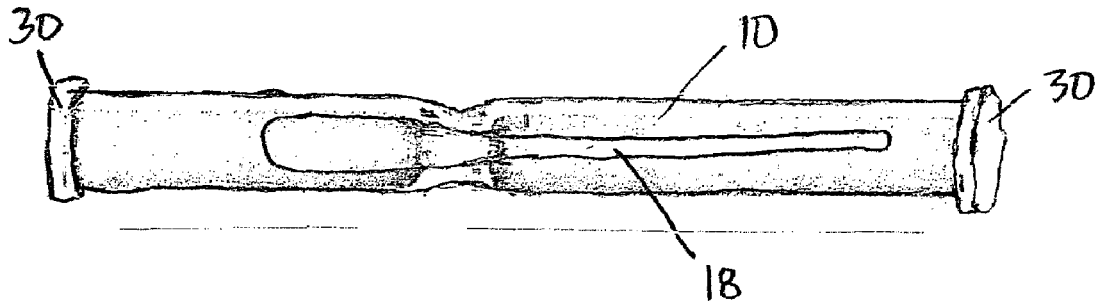
FIG. 5 shows a collection tube whose ends have been fitted with caps so that the collection tube can also serve as a storage vial for transporting an applicator stick to a forensic laboratory for testing.

Also, in some applications, it may be useful to have the ends of the collection tube shaped so that they can accept caps 30. These can be used to close the ends of the collection tube 10 so that it can also function as a storage vial to be used in transporting an applicator stick to a forensic laboratory for testing. See FIG. 5

Figure 6:
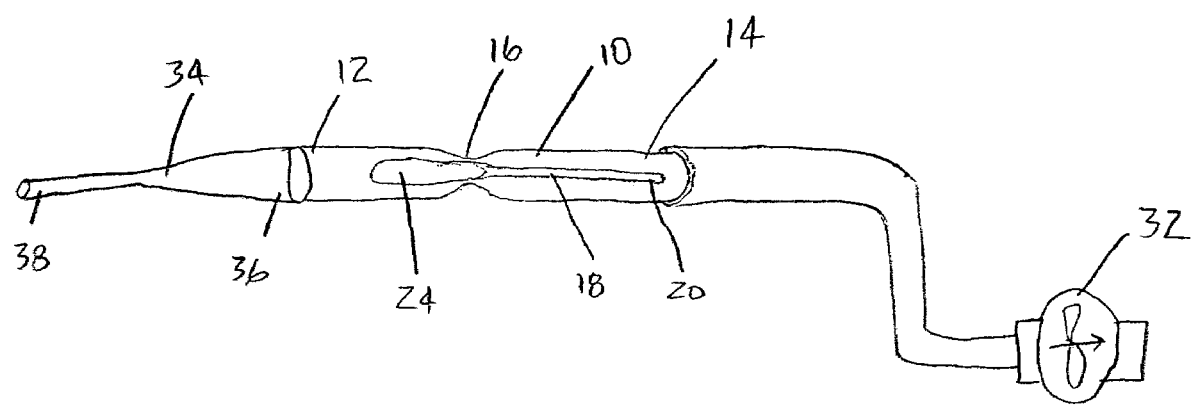
FIG. 6 shows a preferred embodiment for arranging the elements of the present invention when an evidence sample is being collected by applying a vacuum source to the collection tube's downstream end.

This apparatus is used to collect trace evidence samples on the applicator stick's cotton tip 24 by placing the proximate 20 end of the stick in the upstream 12 end of the collection tube 10 and then inserting the whole stick until the base of its cotton tip 24 comes to rest at the beginning of the tube's constriction 16, with the balance of the stick extending through the constriction and approaching the tube's downstream 14 end. A vacuum source 32 is then temporarily applied to the tube's downstream 14 end as the upstream 12 end of the tube 10 is moved over the area of interest so that evidence samples that come within range of the tube's upstream 12 end are sucked into the tube 10 and collected on the stick's air permeable tip 24 which blocks the opening to the tube's constriction 16. See FIG. 6. After an area to-be-searched for evidence has been thoroughly searched with the tube's vacuuming upstream 12 end, the vacuum source 32 is turned off and the applicator stick 18, especially air permeable tip 24, is removed from the collection tube 10 and stored in the test tube 26 or storage vial for later laboratory analysis of the materials collected on the air permeable tip 24.

An especially configured nozzle 34 may be attached to the collection tube 10 and used to aid in concentrating the suction of the vacuum source into a localized area. The downstream end 36 of this nozzle is configured so as to mate with the tube's upstream 12 end, while its upstream 38 end is shaped so as to provide optimal suction in a localized area of interest.

A preferred embodiment of the present invention has been constructed by utilizing these additional design specifications: the collection tube and applicator stick are patterned respectively after a Stock No. 13-678-20A, Fisher Scientific disposable Pasteur pipette having a ASTM E 732 constriction, and a Stock No. 14-959-92B, Fisher Scientific Cotton-Tipped Applicator. A Gast No. DOA P104 AA oil-less diaphragm-type pressure/vacuum pump was operated at a vacuum of 18 inches Hg. to provide the vacuum source for use with the above sized elements. In some applications of this equipment, it proved helpful to apply a drop of distilled water to the upstream end of the collection tube so as to moisten the tip of the downstream applicator stick. This drop of water was found to facilitate the collection of very small particles on the surface of the applicator's cotton tip.

The foregoing descriptions of the invention have been presented for purposes of illustration and description. Further, the description is not intended to limit the invention to the form disclosed herein. Consequently, variations and modifications commensurate with the above teachings, and combined with the skill or knowledge in the relevant art are within the scope of the present invention.

The preferred embodiments described herein are further intended to explain the best mode known of practicing the invention and to enable others skilled in the art to utilize the invention in various embodiments and with various modifications required by their particular applications or uses of the invention. It is intended that the appended claims be construed to include alternate embodiments to the extent permitted by the current art.

I claim:

1. An apparatus for collecting air-transportable evidence samples, said apparatus comprising:
   a collection tube having a specific cross-sectional area, open upstream and downstream ends, and at a specified point between said ends a specified constriction in the cross-sectional area of said tube,
   an applicator stick having proximate and distal ends, the length of said stick being less than the length of said collection tube between said constriction and downstream end, and
   an air permeable, specified diameter, tip located on the distal end of said applicator, the diameter of said tip being less than the diameter of said collection tube and greater than the diameter of said tube constriction.

2. An apparatus as recited in claim 1 wherein said collection tube, applicator stick, and tip are configured so as to allow said evidence sample to be collected on said tip by placing said proximate end of said applicator stick in said upstream end of said tube, and orienting said stick so that said tip is proximate said tube constriction and then imposing a suction force on said downstream end of said tube so that any air-transportable evidence sample proximate said upstream end of said tube is sucked into said tube and becomes lodged on said tip.

3. An apparatus as recited in claim 1 further comprising:
   a nozzle having an upstream end and a downstream end, said downstream end configured so as to allow mating with said collection tube upstream end, said nozzle upstream end configured to aid in the collection of said evidence sample.

4. An apparatus as recited in claim 2 further comprising:
   a nozzle having an upstream end and a downstream end, said downstream end configured so as to allow mating with said collection tube upstream end, said nozzle upstream end configured so aid in the collection of said evidence sample.

5. An apparatus as recited in claim 1 further comprising:
   a test tube having a diameter and length which allows said applicator stick to be stored in said test tube, and
   a test tube cap configured so as to fit onto and seal the open end of said test tube.

6. An apparatus as recited in claim 2 further comprising:
   a test tube having a diameter and length which allows said applicator stick to be stored in said test tube, and
   a test tube cap configured so as to fit onto and seal the open end of said test tube.

7. An apparatus as recited in claim 1 further comprising:
   a test tube having a diameter and length which allows said collection tube to be stored in said test tube, and
   a test tube cap configured so as to fit onto and seal the open end of said test tube.

8. An apparatus as recited in claim 2 further comprising:
   a test tube having a diameter and length which allows said collection tube to be stored in said test tube, and
   a test tube cap configured so as to fit onto and seal the open end of said test tube.

9. An apparatus as recited in claim 1 further comprising:
   a pair of caps, each of said caps configured so as to fit onto and close one of said collection tube ends so that said collection tube can also be used as a storage vial for an applicator stick whose tip may contain trace evidence samples.

10. An apparatus as recited in claim 2 further comprising:
    a pair of caps, each of said caps configured so as to fit onto and close one of said collection tube ends so that said collection tube can also be used as a storage vial for an applicator stick whose tip may contain trace evidence samples.

11. A method for collecting air-transportable evidence samples, said method comprising the steps of:
    utilizing a collection tube having a specific cross-sectional area, open upstream and downstream ends, and at a specified point between said ends a specified constriction in the cross-sectional area of said tube,
    utilizing an applicator stick having proximate and distal ends, the length of said stick being less than the length of said collection tube between said constriction and downstream end,
    wherein said applicator stick having an air permeable, specified diameter, tip located on the distal end of said applicator, the diameter of said tip being less than the diameter of said collection tube and greater than the diameter of said tube constriction,
    placing said proximate end of said applicator stick in said upstream end of said tube,
    orienting said stick in said tube so that said tip is proximate said tube constriction, and
    imposing a suction force on said downstream end of said tube so that any air-transportable evidence sample proximate said upstream end of said tube is sucked into said tube and becomes lodged on said tip.

12. A method as recited in claim 11 further comprising the step of:
    utilizing a nozzle having an upstream end and a downstream end, said downstream end configured so as to allow mating with said collection tube upstream end, said nozzle upstream end configured so aid in the collection of said evidence sample, and
    attaching said nozzle downstream end to said collection tube upstream tube.

13. A method as recited in claim 11 further comprising the step of:
    utilizing a test tube having a diameter and length which allows said applicator stick to be stored in said test tube, and
    storing, after said applicator stick has been used to collect an evidence sample, said applicator stick in said test tube.

14. A method as recited in claim 11 further comprising the step of:
    utilizing a test tube having a diameter and length which allows said collection tube to be stored in said test tube, and
    storing, after said collection tube and applicator stick has been used to collect an evidence sample, said collection tube in said test tube.

15. A method as recited in claim 11 further comprising the step of:
    utilizing a pair of caps, each of said caps configured so as to fit onto and close one of said collection tube ends,
    using said caps to close said collection tube ends so that said collection tube can also be used as a storage vial for an applicator stick whose tip may contain trace evidence samples.

* * * * *